United States Patent
Masumoto et al.

(10) Patent No.: US 9,574,996 B2
(45) Date of Patent: *Feb. 21, 2017

(54) SUCTION-TYPE SMOKE SENSING SYSTEM

(75) Inventors: Shintaro Masumoto, Hachioji (JP); Kazuhisa Itoh, Hachioji (JP); Masao Iguchi, Hachioji (JP); Fumiyoshi Kobayashi, Hachioji (JP); Satoru Nakahata, Hachioji (JP)

(73) Assignee: FENWAL CONTROLS OF JAPAN, LTD., Tokyo (JP)

( * ) Notice: Subject to any disclaimer, the term of this patent is extended or adjusted under 35 U.S.C. 154(b) by 635 days.

This patent is subject to a terminal disclaimer.

(21) Appl. No.: 13/581,855

(22) PCT Filed: Sep. 2, 2011

(86) PCT No.: PCT/JP2011/070023
§ 371 (c)(1),
(2), (4) Date: Aug. 30, 2012

(87) PCT Pub. No.: WO2013/031016
PCT Pub. Date: Mar. 7, 2013

(65) Prior Publication Data
US 2013/0208281 A1   Aug. 15, 2013

(51) Int. Cl.
*G01N 21/00* (2006.01)
*G08B 17/10* (2006.01)
(Continued)

(52) U.S. Cl.
CPC ............. *G01N 21/53* (2013.01); *G08B 17/10* (2013.01); *G08B 17/103* (2013.01); *G08B 17/107* (2013.01); *G08B 17/113* (2013.01)

(58) Field of Classification Search
CPC ..... G08B 17/10; G08B 17/103; G08B 17/107; G01N 21/53; G01N 21/532
(Continued)

(56) References Cited

U.S. PATENT DOCUMENTS

| | | | |
|---|---|---|---|
| 5,587,790 A | 12/1996 | Nagashima | |
| 6,985,081 B2 * | 1/2006 | Wagner | G08B 17/10 169/60 |

(Continued)

FOREIGN PATENT DOCUMENTS

| | | |
|---|---|---|
| CN | 101147053 A | 3/2008 |
| DE | 1154379 | 9/1963 |

(Continued)

OTHER PUBLICATIONS

Search Report in Corresponding Chinese Patent Application No. 201180008618.7 Issued on Mar. 16, 2015; Notice of Reasons for Refusal in Corresponding Japanese Patent Application No. 2012-528977 Issued on Mar. 17, 2015.

(Continued)

*Primary Examiner* — Sunghee Y Gray
(74) *Attorney, Agent, or Firm* — Bacon & Thomas, PLLC

(57) ABSTRACT

This invention relates to a suction-type smoke sensing system which detects smoke with high accuracy and rapidly and identifies a fire occurrence spot quickly.

The system of the present invention is provided with a piping for sucking air in each region to be inspected, a photoelectric smoke sensor which, when air in each of the regions to be inspected is sucked, senses mixing of smoke in the air, and a control unit which sucks the air in the region to be inspected and is electrically connected to the photoelectric smoke sensor so as to receive and process a detection signal. The photoelectric smoke sensor is provided with a smoke sensing portion which senses the smoke in the sucked air, a suction port provided on the air inflow side of the smoke sensing portion, directly sucks the air in the region to be inspected, and fitted with a base end portion of a suction pipe which extends to the region to be inspected, (Continued)

and a fitting portion provided on the air outflow side of the smoke sensing portion and fitted with the end portion of the piping.

10 Claims, 7 Drawing Sheets

(51) Int. Cl.
*G01N 21/53* (2006.01)
*G08B 17/103* (2006.01)
*G08B 17/107* (2006.01)
*G08B 17/113* (2006.01)

(58) Field of Classification Search
USPC ........ 340/628, 630; 356/440, 437, 438, 439, 356/337, 236
See application file for complete search history.

(56) References Cited

U.S. PATENT DOCUMENTS

| | | | |
|---|---|---|---|
| 7,456,961 B2* | 11/2008 | Barton et al. | 356/338 |
| 7,697,140 B2 | 4/2010 | Iguchi et al. | |
| 7,948,627 B2 | 5/2011 | Iguchi et al. | |
| 9,242,130 B2* | 1/2016 | Hennegan | A62C 35/68 |
| 2004/0145484 A1* | 7/2004 | Wagner et al. | 340/628 |
| 2007/0008157 A1* | 1/2007 | Siemens et al. | 340/577 |
| 2010/0176957 A1* | 7/2010 | Iguchi et al. | 340/630 |

FOREIGN PATENT DOCUMENTS

| | | |
|---|---|---|
| JP | H04-5797 A | 1/1992 |
| JP | 06103475 A | 4/1994 |
| JP | 07182574 A | 7/1995 |
| JP | 08263767 A | 11/1996 |
| JP | 09-147255 A | 6/1997 |
| JP | H09147255 A | 6/1997 |
| JP | 6398096 A | 4/1998 |
| JP | 2004220155 A | 8/2004 |
| JP | 2005-309735 A | 11/2005 |
| JP | 2008-287452 A | 11/2008 |
| JP | 2008287452 A | 11/2008 |
| JP | 2009-003510 A | 1/2009 |
| JP | 2009003510 A | 1/2009 |

OTHER PUBLICATIONS

Supplementary European Search Report Issued May 12, 2015 in Corresponding Appl. No. 11861320.7.

* cited by examiner

SUCTION-TYPE SMOKE SENSING SYSTEM

TECHNICAL FIELD

The present invention relates to a suction-type smoke sensing system which sucks air in a region to be inspected and senses smoke when sucking the air.

BACKGROUND ART

The suction-type smoke sensing system is a system which sucks air in a region to be inspected by providing a piping in the region to be inspected and senses mixing of smoke in the air. Examples of this suction-type smoke sensing system include Patent Literature 1. The system of this Patent Literature 1 will be outlined below.

This system is provided with an air sampling pipe having a plurality of air suction holes drilled and laid in a network state, an air sucking apparatus connected to this air sampling pipe and sucking air into the air sampling pipe, a plurality of smoke detectors arranged inside the air sampling pipe in a distributed manner, and a display device for receiving a detection signal from any one of the smoke detectors and displaying the result.

Patent Document 1: Japanese Patent Laid-Open No. 09-147255

DISCLOSURE OF THE INVENTION

Problems to be Solved by the Invention

In the above-described prior-art suction-type smoke sensing system, air in a wide range is sucked by the air sampling pipe and mixing of smoke can be detected by the smoke detector, but if the region to be inspected is segmented or the like, optimal handling becomes difficult.

For example, if there are a large number of small regions to be inspected, even if smoke is detected, the detection site cannot be grasped easily, and a fire occurrence spot cannot be identified easily.

If a distance between the suction hole of the air sampling pipe and the smoke detector is large, smoke is diluted, and smoke detection with high accuracy cannot be made easily.

If there is a large difference in the distances between each of the plurality of suction holes of the air sampling pipe and the smoke detector, a degree of dilution of smoke is different, and detection performance might be different.

If the region to be inspected is large and the distance between the suction hole of the air sampling pipe and the smoke detector is large, it takes time until the smoke is detected, and early discovery of fire becomes difficult.

Moreover, in the case of a special region to be inspected where an amount of smoke generated from fire is small, detection of smoke with high accuracy cannot be made easily.

The present invention is made in view of the above circumstances and provides a suction-type smoke sensing system which can detect smoke and identify a fire occurrence spot with high accuracy and rapidly.

Means to Solve the Problems

In order to solve the above problems, a suction-type smoke sensing system of the present invention is provided with a piping which sucks air in each region to be inspected, a photoelectric smoke sensor which detects smoke mixed in the air when the air in each region to be inspected is sucked, and a control unit which sucks the air in the region to be inspected and is electrically connected to the photoelectric smoke sensor so as to receive and process a detection signal. The photoelectric smoke sensor is provided with a smoke sensing portion which senses smoke in the sucked air, a suction port provided on the air inflow side of the smoke sensing portion, directly sucking the air in the region to be inspected and fitted with a base end portion of a suction pipe extending to the region to be inspected, and a fitting port provided on the air outflow side of the smoke sensing portion and fitted with an end portion of the pipe.

Effect of the Invention

According to the present invention, smoke can be detected with high accuracy and rapidly. Moreover, since a fire occurrence spot can be identified rapidly, quick response can be made.

Figure 1:
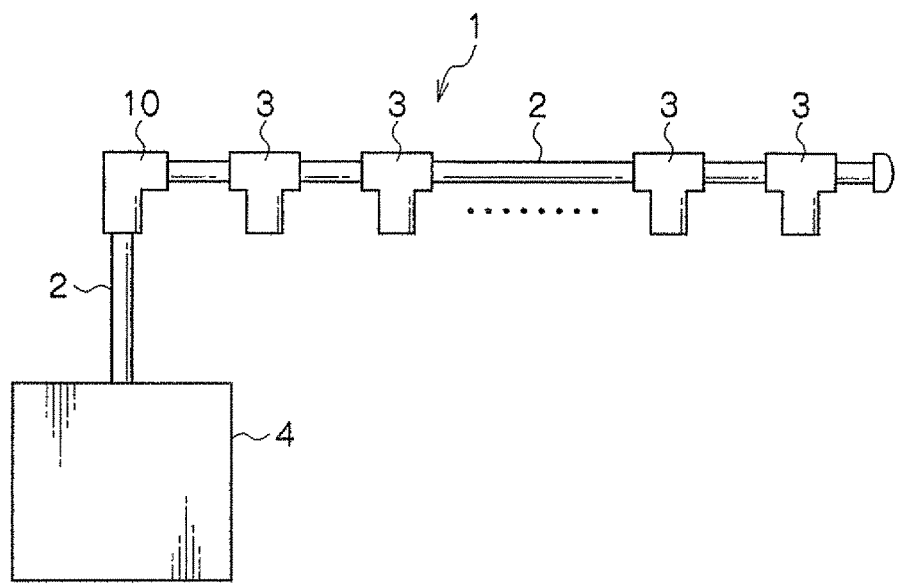
FIG. 1 is a configuration diagram illustrating a suction-type smoke sensing system of a first embodiment of the present invention.

EXPLANATIONS OF REFERENCE NUMERALS 1 suction-type smoke sensing system
2 sampling pipe
3 photoelectric smoke sensor
4 control unit
6 smoke sensing portion
7 suction port
8 fitting port
9 suction pipe
10 connection pipe
12 space 13 space
14 air inlet
16 housing
16a inner wall on detection region side
17 light emitting element
18 light receiving element
19, 20 reflecting member
19a, 20a reflecting surface
21 light emitting element accommodation portion
22 optical window portion
23 light receiving element accommodation portion
23a projection portion
24 objective lens
25 shielding plate
27, 28 labyrinth piece
27a projection portion
31 light emitting element
32 light receiving element
33 shielding plate
34 lens
35 light receiving element accommodation portion
35a inclined member
35b inclined surface
37 reflecting member
37a reflecting surface
38 reflecting member
38a reflecting surface

BEST MODE FOR CARRYING OUT THE INVENTION (A) First Embodiment

A first embodiment of the present invention will be described below. A suction-type smoke sensing system of the present invention is a system which specifies a region to be inspected and senses smoke in the region with high accuracy and rapidly. This suction-type smoke sensing system sucks air in each region to be inspected, respectively, and senses smoke when sucking the air.

The suction-type smoke sensing system 1 mainly includes, as illustrated in FIG. 1, a sampling pipe 2, a photoelectric smoke sensor 3, and a control unit 4. If the suction-type smoke sensing system 1 is specifically installed in each region to be inspected, there can be a required configuration other than the above-described configuration, but since they are all known configurations, explanation will be omitted here. The same applies to the following.

The sampling pipe 2 is a pipe disposed facing the region to be inspected for sucking air in this region to be inspected. The sampling pipe 2 is disposed in accordance with the region to be inspected. The number of the regions to be inspected might be one or plural. The sampling pipe 2 is disposed in accordance with these regions to be inspected. The sampling pipe 2 is formed of a pipe member having a plurality of lengths.

Moreover, a suction pipe 9 (See FIG. 4) might be provided from the sampling pipe 2 to the region to be inspected. As a result, the sampling pipe 2 is assembled on each fitting port 8 of the photoelectric smoke sensor 3 which will be described later and the suction pipe 9 is connected to a suction port 7 of the photoelectric smoke sensor 3 which will be described later as appropriate into a piping configuration in accordance with the various regions to be inspected.

There are various piping configurations of this sampling pipe 2 and one of them is an L-shaped piping configuration as illustrated in FIG. 1. The sampling pipe 2 is connected to the both sides of an L-shaped connection pipe 10 and is bent in the L-shape so as to have the L-shaped piping configuration. A control unit 4 is connected to the sampling pipe 2 on the base end side of the connection pipe 10. The sampling pipe 2 and the photoelectric smoke sensor 3 are connected alternately to the distal end side of the connection pipe 10. Specifically, the sampling pipe 2 is connected to each fitting port 8 of the photoelectric smoke sensor 3 so as to configure the piping in accordance with the region to be inspected. The sampling pipe 2 might be connected longer in accordance with the region to be inspected. The connection pipe 10 or connection pipes having other angles might be used at the distal end side of the connection pipe 10 so as to meander the sampling pipe 2 in accordance with the region to be inspected.

Figure 3:
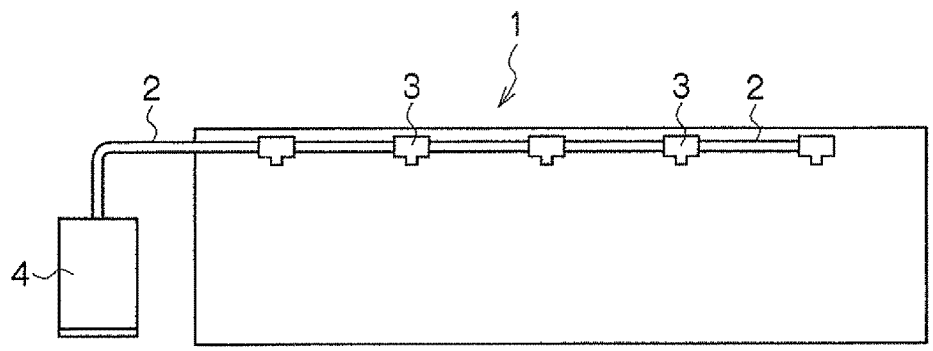
FIG. 3 is a configuration diagram illustrating a piping configuration example of the suction-type smoke sensing system of the present invention.

Moreover, if the region to be inspected is a large space as illustrated in FIG. 3, a plurality (5 units in FIG. 3) of the photoelectric smoke sensors 3 are installed by being connected with the sampling pipe 2 at certain intervals.

Figure 4:
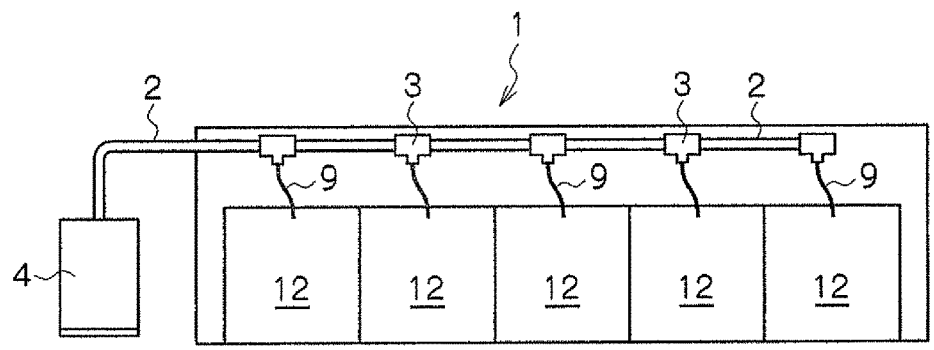
FIG. 4 is a configuration diagram illustrating a piping configuration example of the suction-type smoke sensing system of the present invention.

Moreover, if the region to be inspected is divided into small spaces 12 such as power receiving facilities disposed in plural as in FIG. 4, the suction pipe 9 is connected to the suction port 7 of each of the photoelectric smoke sensors 3, and each suction pipe 9 is extended into each space 12.

Figure 5:
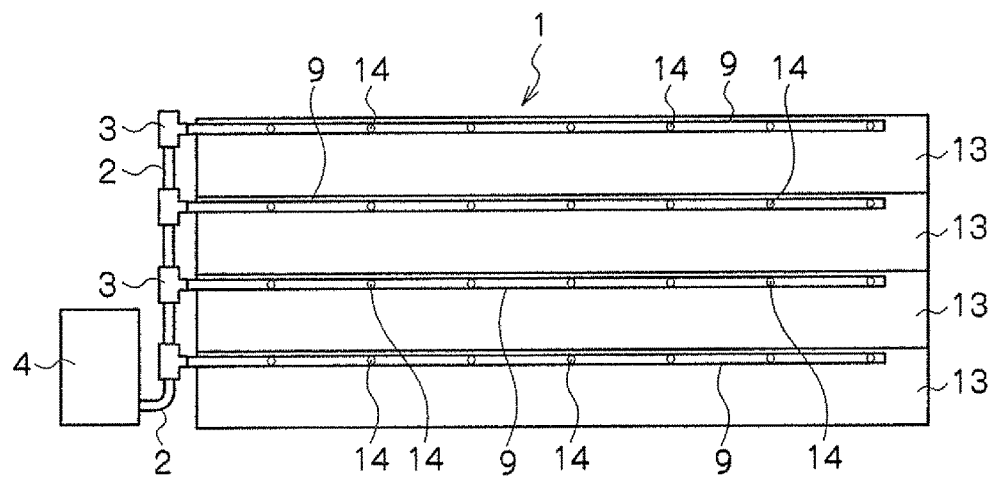
FIG. 5 is a configuration diagram illustrating a piping configuration example of the suction-type smoke sensing system of the present invention.

If the region to be inspected is configured by stacking laterally-wide and vertically-small spaces 13 in plural stages as in FIG. 5, the photoelectric smoke sensor 3 is disposed so as to be located in each space 13. Specifically, each photoelectric smoke sensor 3 is connected by the sampling pipe 2 to each other, the suction pipe 9 is connected to the suction port 7 of each photoelectric smoke sensor 3, respectively, and each suction pipe 9 is disposed in each space 13. In each suction pipe 9, air inlets 14 are provided at certain intervals.

Other than the above, various piping configurations are possible. That is, various piping configurations can be realized by arranging each of the photoelectric smoke sensors 3 in accordance with the region to be inspected and by connecting these photoelectric smoke sensors 3 and the control unit 4 by the sampling pipe 2 as appropriate.

The photoelectric smoke sensor 3 is an apparatus which senses mixing of smoke in air when the control unit 4 sucks the air in each region to be inspected via the sampling pipe 2. The photoelectric smoke sensor 3 is attached to the sampling pipe 2 while being faced with each of the above-described regions to be inspected. Moreover, the photoelectric smoke sensor 3 has a function as connecting means for connecting a plurality of the sampling pipes 2 constituting the piping of the suction-type smoke sensing system 1 as appropriate. An address is set to each of the photoelectric smoke sensor 3, respectively. The control unit 4 can accurately identify the position of the photoelectric smoke sensor 3 by this address. As means for setting an address to each of the photoelectric smoke sensor 3, any of the known means can be used.

Figure 2:
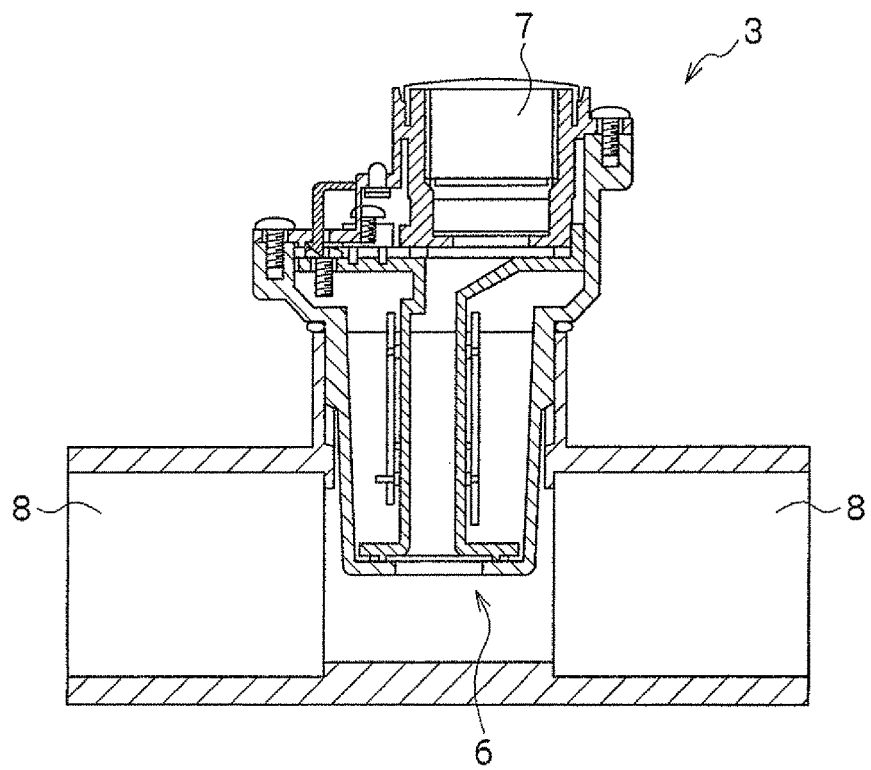
FIG. 2 is a sectional view illustrating a photoelectric smoke sensor of a first embodiment of the present invention.

The photoelectric smoke sensor 3 mainly includes, as illustrated in FIG. 2, a smoke sensing portion 6, a suction port 7, and a fitting port 8.

The smoke sensing portion 6 is an apparatus for sensing smoke in the sucked air. A specific configuration of this smoke sensing portion 6 will be described later.

The suction port 7 is an opening for directly sucking the air in the region to be inspected. Moreover, the suction port 7 is an opening for fitting the base end portion of the suction pipe 9 disposed by being extended to the region to be inspected. This suction port 7 is provided on the air inflow side of the smoke sensing portion 6.

The suction port 7 is formed cylindrically, and one of the ends thereof is opened. This suction port 7 is provided so as to open toward the region to be inspected and sucks the peripheral air. If the suction pipe 9 is fitted in the suction port 7, the air around the distal end opening of this suction pipe 9 is sucked. The suction port 7 is connected to the smoke sensing portion 6. As a result, when the air is sucked from the smoke sensing portion 6 side, the air in the periphery of the suction port 7 or the periphery of the distal end opening of the suction pipe 9 is sucked and flows into the smoke sensing portion 6.

The fitting port 8 is an opening which fits in the end portion of the sampling pipe 2 so as to create the piping configuration of the suction-type smoke sensing system 1. The fitting port 8 is provided on the air outflow side of the smoke sensing portion 6. The fitting port 8 might be provided singularly on the air outflow side of the smoke sensing portion 6 but two fitting ports are provided oppositely here. The sampling pipe 2 is connected to these two fitting ports 8 as appropriate. Moreover, the suction pipe 9 is connected to the suction port 7 as appropriate. As a result, the piping configuration in accordance with various regions to be inspected as illustrated in FIGS. 3 to 5 can be assembled.

The control unit 4 is a device which mainly sucks the air in the region to be inspected and processes a detection signal. The control unit 4 might be provided with other functions but is mainly provided with the above two functions here. That is, the control unit 4 is mainly provided with functions as a suction apparatus (not shown) which is connected to the base end portion of the sampling pipe 2 and sucks air in the region to be inspected and a smoke detecting apparatus which is electrically connected to the photoelectric smoke sensor 3 and detects presence of smoke by receiving a detection signal. The control unit 4 is electrically connected to a light receiving element 18 of the smoke sensing portion 6. Specifically, a signal line (not shown) is disposed separately from the sampling pipe 2, and the light receiving element 18 of each smoke sensing portion 6 and the control unit 4 are electrically connected. As a result, the control unit 4 grasps the position of each smoke sensing portion 6.

The smoke sensing portion 6 is an apparatus which detects smoke accompanying fire occurrence. The smoke sensing portion 6 was made to be able to handle a special apparatus by improving sensitivity to the smoke. Specifically, the smoke sensing portion 6 can handle not only general households and places where people gather such as public facilities but also special apparatuses such as a semiconductor manufacturing apparatus, a machine tool, a power distribution panel, an industrial controller and the like in a plant. Particularly, the smoke sensing portion 6 was made to be able to handle an apparatus which cannot easily generate smoke or generates less smoke even if fire breaks out.

Figure 6:
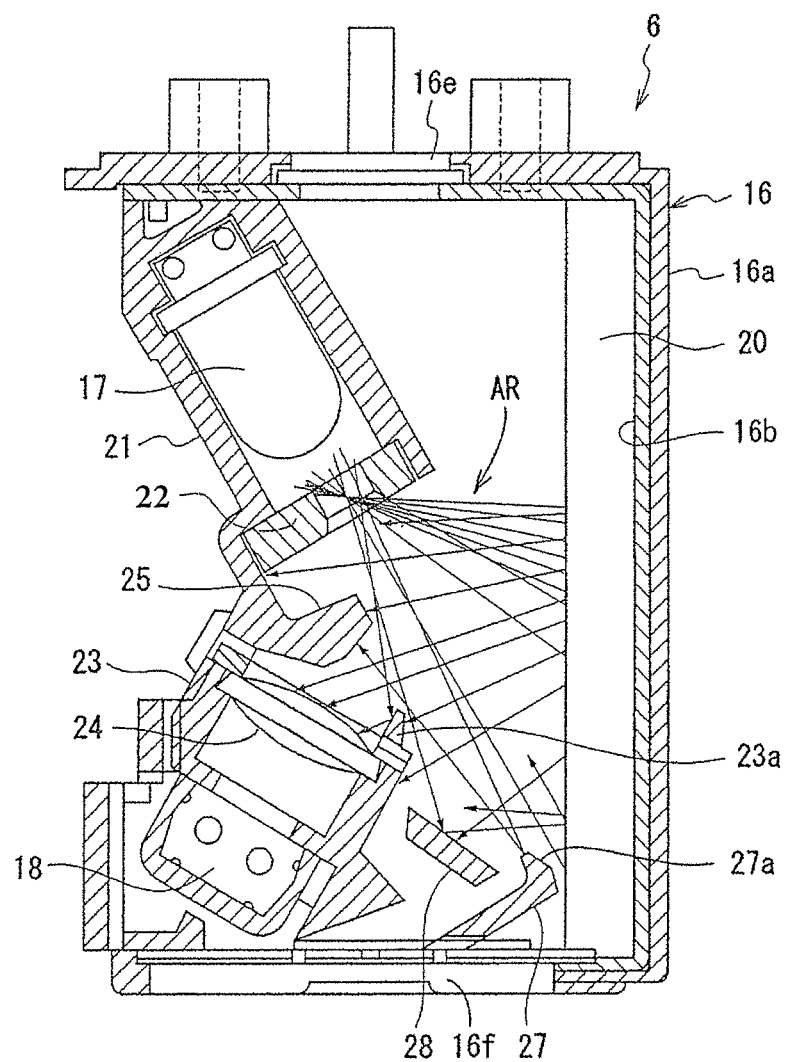
FIG. 6 is a side sectional view illustrating the smoke sensing portion of the first embodiment of the present invention.
Figure 7:
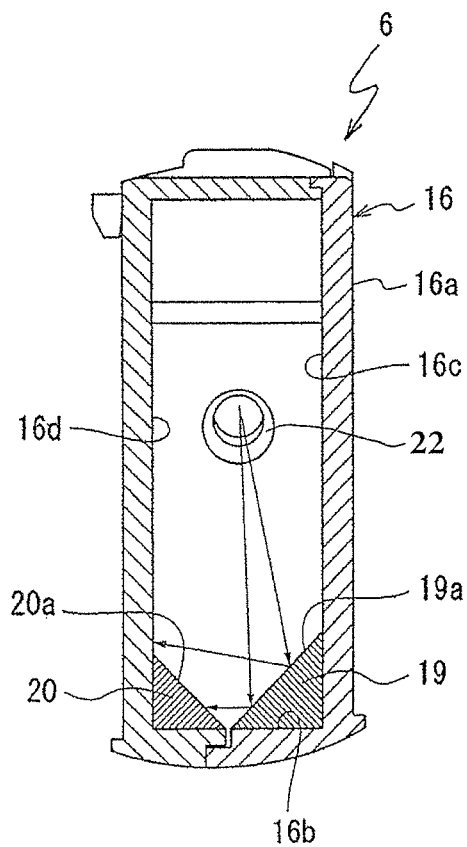
FIG. 7 is a plan sectional view of the smoke sensing portion in FIG. 6.

The smoke sensing portion 6 detects smoke flowing into a housing of the photoelectric smoke sensor 3 by light. Since the photoelectric smoke sensor 3 is disposed in the region to be inspected with the sampling pipe 2 connected, the size thereof needs to be small. Thus, the smoke sensing portion 6 was configured having a small size. Specifically, the smoke sensing portion 6 mainly includes the housing 16, a light emitting element 17, the light receiving element 18, and reflecting members 19 and 20 as illustrated in FIGS. 6 and 7.

The housing 16 is a member for allowing the air in which smoke is mixed to flow inside. The housing 16 is provided with the light emitting element 17, the light receiving element 18, and the reflecting member 19 therein. A ventilation hole 16e communicating with the suction port 7 is provided in the upper part of the housing 16. Moreover, a ventilation hole 16f communicating with the fitting port 8 is provided in the lower part of the housing 16.

The light emitting element 17 is an element for emitting inspection light to a smoke detection region AR. The light emitting element 17 is provided by facing the smoke detection region AR in the housing 16. The light emitting element 17 is provided at a position in the upper part (upper left in FIG. 6) of the internal space of the housing 16 by a light emitting element accommodation portion 21. The light emitting element accommodation portion 21 accommodates the light emitting element 17 so that the inspection light emitted from the light emitting element 17 is emitted only forward. An optical window portion 22 is provided in the front of the light emitting element accommodation portion 21.

The light receiving element 18 is an element which detects smoke by receiving diffused light diffused when the inspection light from the light emitting element 17 hits the smoke. The light receiving element 18 is provided at a position deviated from an optical path of the inspection light of the light emitting element 17 while facing the detection region AR. Specifically, the light receiving element 18 is provided at a position lower left in the internal space of the housing 16 by a light receiving element accommodation portion 23. The light receiving element accommodation portion 23 accommodates the light receiving element 18 at a bottom part thereof and has an objective lens 24 attached above that. On an opening portion of the light receiving element accommodation portion 23, a projection portion 23a which prevents the diffused light from entering the light receiving element 18 is provided.

The light receiving element 18 receives the diffused light diffused when the inspection light hits the smoke and detects the smoke. Specifically, the optical axis of the light emitting element 17 and the optical axis of the light receiving element 18 are disposed so as to cross each other at an angle of substantially 120 degrees, and the vicinity of the intersection is the smoke detection region AR. As a result, if there is smoke in the detection region AR, the inspection light from the light emitting element 17 is diffused by the smoke, and the diffused light reaches the light receiving element 18, and presence of the smoke is detected.

The light receiving element 18 detects the smoke by incidence of the diffused light but specifically, when an incidence amount of the diffused light exceeds a threshold value, an inspection signal notifying that the smoke is sensed is transmitted to the control unit 4. The light receiving element 18 can adjust the threshold value by means of control of the control unit 4. As a result, the light receiving element 18 can make adjustment from setting with an ordinary threshold value for sensing the smoke with high accuracy to the setting with a raised threshold value and lowered accuracy for sensing the smoke with low accuracy. This function of adjusting the accuracy may be provided in the control unit 4. Specifically, the threshold value is set in the control unit 4, and if the incidence amount of the diffused light in the light receiving element 18 is changed, it is set that the detection signal is transmitted to the control unit 4 regardless of the magnitude of the incidence amount. Then, the control unit 4 detects generation of smoke by discriminating the detection signal from the light receiving element 18 by the threshold value. Then, this threshold value is made adjustable.

A shielding plate 25 is provided between the light emitting element 17 and the light receiving element 18 (at a position in the left to the detection region AR), and the shielding plate 25 prevents the inspection light from the light emitting element 17 from directly entering the light receiving element 18 without being diffused.

In the right of the light receiving element accommodation portion 23, two labyrinth pieces 27 and 28 are provided. The labyrinth piece 27 is formed with inclination in the upper right direction so as to guide an air flow from the lower side by the lower face thereof in the upper right direction. Moreover, an end portion in the upper direction of the labyrinth piece 27 is bent in the upper left direction. The labyrinth piece 28 is formed with inclination in the upper left direction at an upper left position with respect to the labyrinth piece 27. These labyrinth pieces 27 and 28 prevent intrusion of ambient light.

The reflecting members 19 and 20 are members which deviate and reflect the inspection light emitted from the light emitting element 17 from this light receiving element 18 so that the inspection light does not enter the light receiving element 18. The reflecting members 19 and 20 are provided on an inner wall 16*a* on the detection region side of the housing 16 at positions opposing the light emitting element 17 while sandwiching the detection region AR (See FIG. 6) between them. The reflecting members 19 and 20 are, as illustrated in FIG. 6, provided on the whole region in the vertical direction of the inner wall 16*a* on the detection region side. Moreover, the reflecting members 19 and 20 are, as illustrated in FIG. 7, provided with reflecting surfaces 19*a* and 20*a* having a planar shape inclined in the V-shape. The reflecting surfaces 19*a* and 20*a* are surfaces which deviate and reflect the inspection light emitted from the light emitting element 17 from the light receiving element 18 in a direction not toward the light receiving element 18. The reflecting surface 19*a* is formed larger than the reflecting surface 20*a*. The reflecting surface 19*a* is provided on one side wall surface 16*c* side of the housing 16 and occupies a wide area. The reflecting surface 20*a* is provided on the other side wall surface 16*d* side of the housing 16 and occupies an area smaller than the reflecting surface 19*a*. As a result, the inspection light emitted from the light emitting element 17 is reflected on the two reflecting surfaces 19*a* and 20*a* irregularly. By reflecting the inspection light on the two reflecting surfaces 19*a* and 20*a* irregularly, the reflected light is reflected not toward the light receiving element 18 (deviated from the light receiving element 18) as in FIG. 7. Areas and inclination angles of the two reflecting surfaces 19*a* and 20*a* are set in relation to the light emitting element 17 so that the reflected light does not go toward the light receiving element 18.

Some of the reflected light is reflected twice on the reflecting surfaces 19*a* and 20*a* in the V-shape and changes the direction by 180 degrees. However, if the inspection light is reflected twice, brightness is drastically attenuated and the light amount is drastically decreased. Thus, even if the reflected light reflected twice (hereinafter referred to as secondary reflected light) enters the light receiving element 18, it is not a problem since the light is extremely weak.

Moreover, portions other than the above-described configuration are not particularly limited. Configurations which can be incorporated in the photoelectric smoke sensor of the present invention (peripheral configuration of conventional photoelectric smoke sensors) can be all applied to the present invention.

The suction-type smoke sensing system 1 configured as above acts as follows.

The control unit 4 is operated, and air in the region to be inspected is sucked from the suction port 7 through the sampling pipe 2. If the suction pipe 9 is connected to the suction port 7, the air inside the power distribution panel or the like is sucked from the distal end of the suction pipe 9. The sucked air flows into the smoke sensing portion 6.

In the smoke sensing portion 6, the inspection light emitted from the light emitting element 17 toward the detection region AR penetrates the detection region AR and irradiates the reflecting members 19 and 20. Moreover, some inspection light irradiates the side wall surfaces 16*c* and 16*d*, but this light is reflected by the side wall surfaces 16*c* and 16*d* and irradiates the reflecting members 19 and 20.

The reflecting members 19 and 20 reflect the light irregularly on the reflecting surfaces 19*a* and 20*a* in the V-shape and eliminate reflected light toward the light receiving element 18. A part of the reflected light goes toward the light receiving element 18, but it is not a problem since such light is reflected twice or more as described above and is drastically attenuated.

The reflected light reflected by the reflecting surfaces 19*a* and 20*a* irradiate the side wall surfaces 16*c* and 16*d*. Then, most of the reflected light reflected by the reflecting surfaces 20*a* and 19*a* irradiates the side wall surfaces 16*c* and 16*d* and is reflected by the side wall surfaces 16*c* and 16*d*. Moreover, most of the reflected light reflected by the side wall surfaces 16*c* and 16*d* also irradiate the opposing side wall surfaces 16*c* and 16*d* and is reflected again. As a result, the reflected light of the inspection light gathers in the periphery of the detection region AR and repeats reflection and most of the light does not enter the light receiving element 18 any longer.

If smoke intrudes from the outside in this state and reaches the vicinity of the detection region AR, the inspection light from the light emitting element 17 hits the smoke and is diffused, and the diffused light enters the light receiving element 18 and the light receiving element 18 detects the smoke. At this time, since the reflected light is also distributed in the periphery of the detection region AR, the diffusion light is also generated in this portion, and the diffused light in the housing 16 increases.

As a result, incidence of the reflected light which becomes noise into the light emitting element 17 can be drastically decreased, and at the same time, the diffused light by the smoke can be increased, and thus, the light receiving element 18 can sense the smoke with higher accuracy.

If sensitivity of the smoke sensing portion 6 is lowered, the smoke is sensed when a large quantity of smoke is generated by fire.

When the smoke sensing portion 6 senses the smoke, a detection signal is transmitted to the control unit 4. Since the control unit 4 grasps the position of the smoke sensing portion 6 which sensed the smoke by the address, upon reception of the detection signal, the control unit 4 identifies occurrence of fire and the position of the fire. And the control unit 4 displays or transmits the occurrence of the fire and positional information as necessary.

As a result, the smoke sensing portion 6 with the sensitivity according to the situation of the region to be inspected can detect presence of generation of smoke immediately in the region to be inspected and discover fire in an early stage.

With a smoke sensing system using a prior-art sampling pipe, if the number of sampling holes is increased, smoke is diluted, and it takes time from generation of smoke to detection of smoke. Moreover, if the piping length of the sampling pipe is long, it takes time for the smoke to reach the smoke sensor, and detection time is delayed. For example, if alarm sensitivity is set to 0.2%/m and 30 sampling holes are provided as an example of the smoke sensing system, smoke was not sensed and an alarm was not issued even at the closest location to the smoke sensor until smoke with concentration of 0.75%/m was sucked through 6 holes. At the terminal end portion the farthest from the smoke sensor, the number of holes required for sensing the smoke and issuing the alarm was further increased. Particularly, in the case of the whole piping length of 45 m, 8 holes were required for issuing an alarm, and it took an extremely long time of 1 minute and 20 seconds to sense the smoke.

On the other hand, with the suction-type smoke sensing system 1 of this embodiment, since the sampling holes in the sampling pipe are replaced by the photoelectric smoke sensor 3, it becomes possible to directly sense the smoke by the neighboring photoelectric smoke sensor 3 in a site where smoke was generated. Thus, there is no problem of dilution of smoke caused by an increase in the number of sampling holes or delay in detection time caused by prolongation of the piping length of the sampling pipe. However longer the sampling pipe is formed, there is no problem of delay in the detection time. Moreover, since each of the photoelectric smoke sensors 3 has its own address, the spot where the smoke is generated can be easily identified.

That is, smoke can be detected with high accuracy and rapidly and a spot of fire occurrence can be identified.

Moreover, if the region to be inspected is a factory or the like, for example, where some smoke can be generated in a usual work, appropriate smoke detection according to the situation of the region to be inspected becomes possible by raising the above-described threshold value so as to lower the sensitivity of the smoke sensing portion 6.

As a result, smoke can be detected with high accuracy and rapidly and a fire occurrence spot can be identified while the device is kept small to the size of the conventional photoelectric smoke sensor.

(B) Second Embodiment

Subsequently, a second embodiment of the present invention will be described.

In this embodiment, the smoke sensing portion 6 of the photoelectric smoke sensor 3 is improved. Specifically, the light source, the shielding plate, and the projection portion of a labyrinth and the like of the smoke sensing portion 6 are improved.

Figure 8:
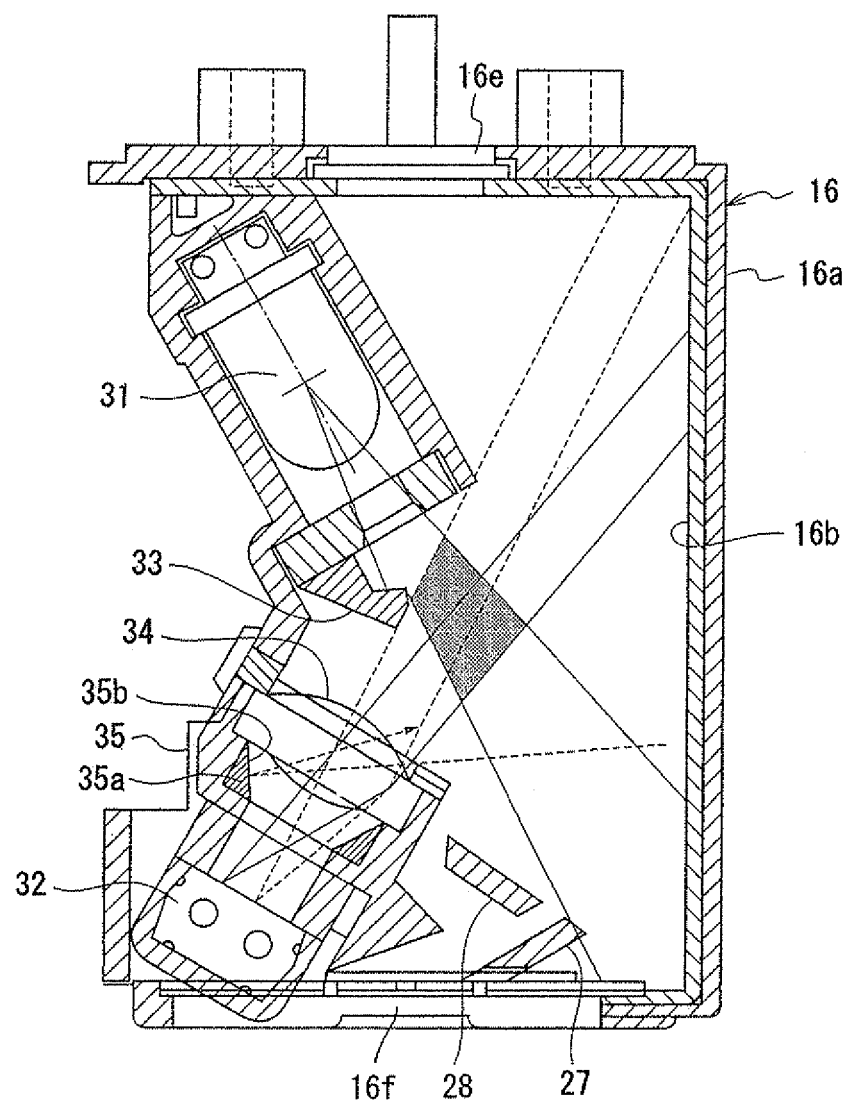
FIG. 8 is a side sectional view illustrating the smoke sensing portion of a second embodiment of the present invention.
Figure 9:
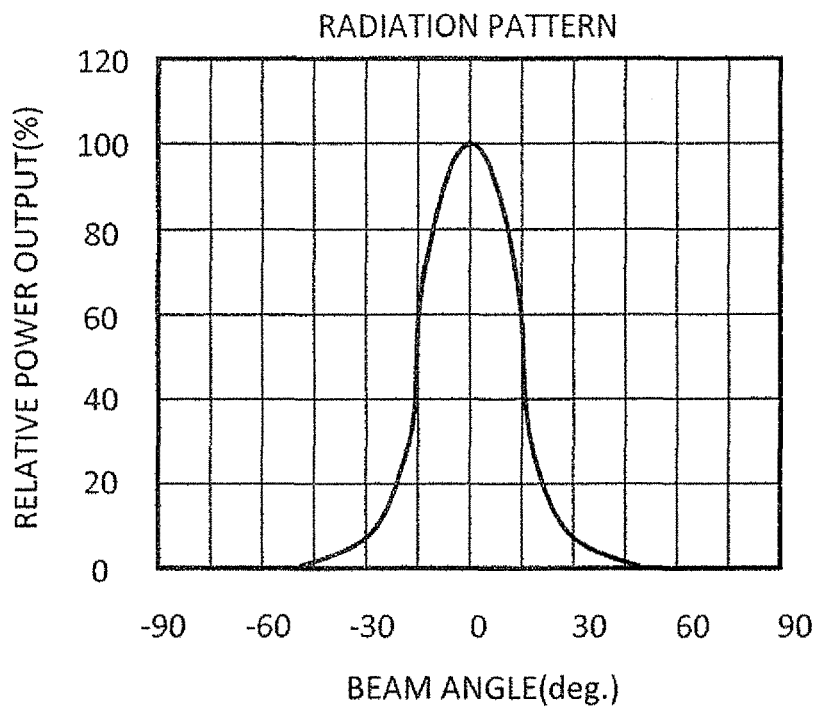
FIG. 9 is a graph illustrating characteristics of a light source of a light emitting element of a prior-art photoelectric smoke sensor.
Figure 10:
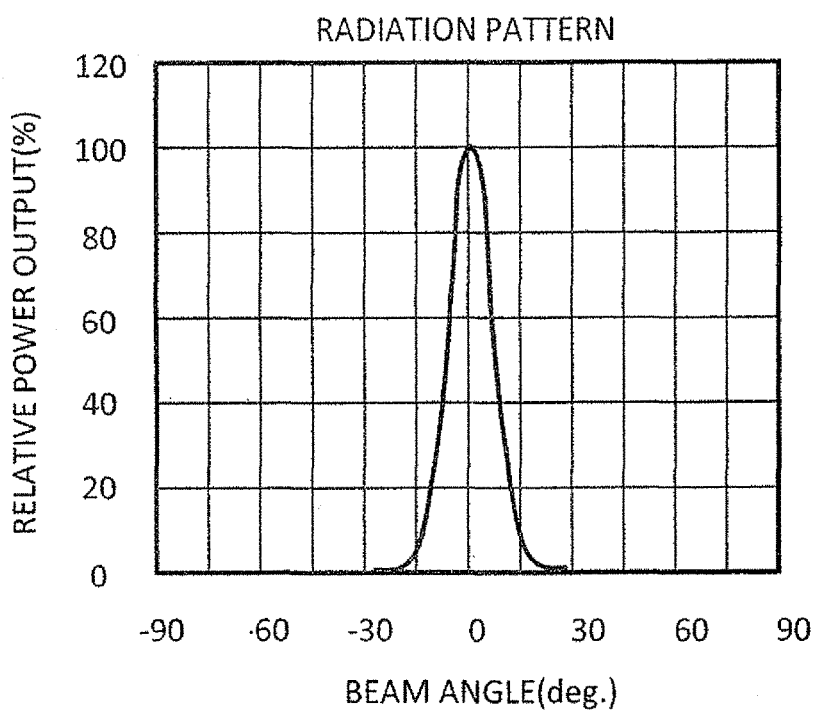
FIG. 10 is a graph illustrating characteristics of a light source of a photoelectric smoke sensor of the second embodiment of the present invention.

In this embodiment, as illustrated in FIG. 8, a light amount of the light source of the above-described light emitting element 31 is increased. Moreover, directivity of the light source is enhanced. An exit angle of the inspection light is narrowed. Specifically, the directivity is enhanced as in FIG. 10 as compared with the prior-art light source in FIG. 9 so as to have a thin light. That is, the inspection light was made thinner and stronger than the prior-art inspection light.

The shielding plate 33 in FIG. 8 is a member provided between the light emitting element 31 and the light receiving element 32 and prevents incidence of the inspection light from the light emitting element 31 directly into the light receiving element 32.

The shielding plate 33 is provided on the light emitting element 31 side so as to get closer to this light-emitting element 31 side and away from the light receiving element 32.

The light receiving element 32 is configured so that the light receiving element 32 is brought far away from the shielding plate 33 by reducing the focal distance of a lens 34 so as to make the whole length of the light receiving element accommodation portion 35 short. As a result, the front of the light receiving element 32 is widened, and the light incident angle is widened. This light incident angle is an angle at which the light can enter, that is, an incident angle of the diffused light which enters into the light receiving element 32. By widening this light incident angle, an amount of diffused light that can be taken into the light receiving element 32, that is, a signal amount is increased.

An inclined member 35*a* is provided inside the lens 34 in the light receiving element accommodation portion 35. The inclined member 35*a* is disposed so as to cover a peripheral edge portion of the lens 34 from inside. A conical (tapered) inclined surface 35*b* is provided on the surface of the inclined member 35*a*. This inclined surface 35*b* is a reflecting surface for reflecting the reflected light incident into the light receiving element accommodation portion 35 to the outside of the light receiving element accommodation portion 35. If the inspection light from the light emitting element 31 is reflected in the housing 16, most of the reflected light is shielded by the shielding plate 33 and the like, but a part thereof might enter the light receiving element accommodation portion 35. Such reflected light enters the periphery of the lens 34 in many cases. Thus, the inclined surface 35*b* provided in the periphery of the lens 34 reflects the reflected light incident into the light receiving element accommodation portion 35 to the outside and prevents incidence into the light receiving element 32. It is only necessary that this inclined surface 35*b* can reflect light but may be mirror-finished for more efficient reflection.

Moreover, a projection portion 27*a* of the labyrinth piece 27 and the projection portion 23*a* in the opening of the light receiving element 18 are eliminated. That is because it is likely that these projection portions 27*a* and 23*a* reflect the inspection light and allow it incident to the light receiving element 32.

In the smoke sensing portion 6 in the above configuration, if smoke flow into the detection region AR, the inspection light which is strong light hits this smoke and generates diffused light. This diffused light is strong in proportion to the inspection light and enters the light receiving element 32.

Moreover, since the light receiving element 32 has a wider light incident angle, it takes in more diffused light and detects the smoke.

As a result, an amount of reflected light incident to the light receiving element 32, which causes noise, can be drastically decreased, and diffused light incident to the light receiving element 32 can be increased, and thus, smoke can be detected with higher accuracy.

As a result, the actions and effects similar to those in the first embodiment can be exerted.

(C) Variation

In the invention according to each of the above-described embodiments, the smoke sensing portion 6 is configured to include components such as the reflecting members 19 and 20 and the like, but not limited to the smoke sensing portion 6 in the first embodiment and the second embodiment, all the configurations of the smoke sensing portion in the first embodiment and the smoke sensing portion in the second embodiment may be combined. Other combinations will also do. Any one or two or more of the components constituting the invention described in each of the above-described embodiments may be combined as appropriate in order to configure the smoke sensing portion 6. In this case, too, the actions and effects similar to those in the above-described embodiments can be exerted.

Figure 11:
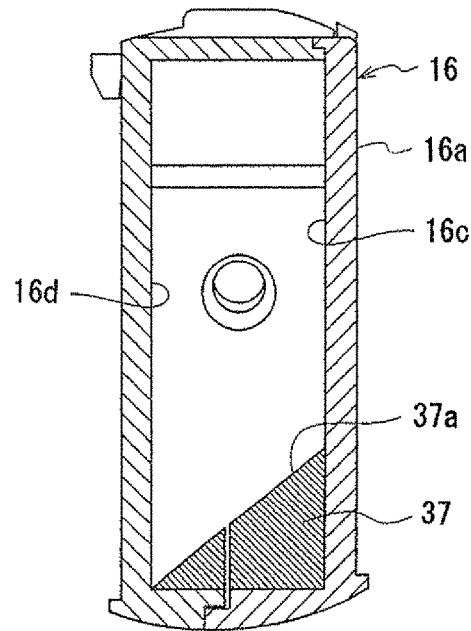
FIG. 11 is a plan sectional view of a photoelectric smoke sensor according to a first variation of the present invention.

In the first embodiment, the reflecting surfaces 19*a* and 20*a* are provided in the V-shape by the reflecting members 19 and 20 of the smoke sensing portion 6, but as illustrated in FIG. 11, one reflecting surface 37a can be provided by one large reflecting member 37. As a result, the inspection light is reflected by the reflecting surface 37a and all irradiates the side wall surface 16d and is reflected by this side wall surface 16d. Then, secondary reflected light is drastically attenuated. In this case, too, the actions and effects similar to those in the first embodiment can be exerted.

Figure 12:
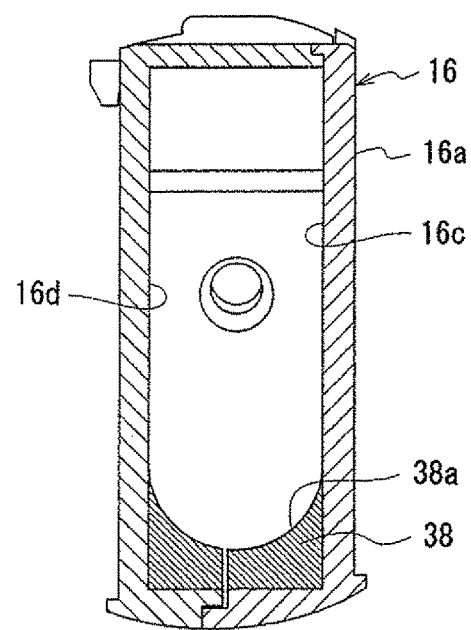
FIG. 12 is a plan sectional view of a photoelectric smoke sensor according to a second variation of the present invention.

Moreover, as illustrated in FIG. 12, a curved reflecting surface 38a may be provided by the reflecting member 38. Furthermore, the reflecting surface 38a may be formed so that the reflected light gathers in the detection region AR and its periphery like a concave mirror of a reflecting telescope. That is, the reflecting surface 38a may be configured to be curved so that the inspection light and the reflected light gather in the detection region AR and its periphery and more diffused light by the smoke flowing into the housing 16 can be generated. In this case, the reflecting surface 38a may be formed as a mirror surface. By forming the reflecting surface 38a as a mirror surface, more reflected light can be gathered to the detection region AR and its periphery.

By these configurations, smoke can be detected with higher accuracy.

In each of the above-described embodiments, the example in which a plurality of the photoelectric smoke sensors 3 are provided is explained, but the suction-type smoke sensing system 1 of the present invention can be also used even if there is only one photoelectric smoke sensor 3.

In each of the above-described embodiments, since sensitivity of each of the photoelectric smoke sensor 3 can be adjusted individually, the sensitivity can be adjusted to the optimum in accordance with the situation of each region to be inspected. For example, in a place where smoke not relating to fire can usually occur, the sensitivity is lowered. In a place where smoke other than fire does not occur at all, the sensitivity is raised. Particularly, in a place where little smoke occurs even if fire breaks out, the sensitivity is raised to the maximum. If there are a plurality of regions to be inspected in one place and the situation of each region to be inspected is different from each other, the sensitivity of each photoelectric smoke sensor 3 is adjusted in accordance with the respective situation of the regions to be inspected. As a result, an optimal smoke sensing system can be constructed.

In each of the above-described embodiments, the control unit 4 is explained as an apparatus having a function of detecting smoke and the like, but other than that, the control unit 4 may include a display portion for displaying fire occurrence and an occurrence position. As a result, a worker can easily grasp where the fire occurred, whereby quick firefighting activities are enabled.

Moreover, the control unit 4 may include an alarm for notifying occurrence of fire. A transmitter for notification to another place may be provided. As a result, quick firefighting activities are enabled.

The invention claimed is:

1. A suction-type smoke sensing system comprising:
   a piping which passes a plurality of regions to be inspected, and sucks air in each of the regions to be inspected;
   a photoelectric smoke sensor which is attached to the piping, at least one said photoelectric smoke sensor being provided for each of the regions to be inspected to detect smoke mixed in the air when the air in each of the regions to be inspected is sucked through a respective said smoke detector; and
   a control unit which is connected to a base end portion of the piping and sucks the air in the region to be inspected and is electrically connected to the photoelectric smoke sensor so as to receive and process a detection signal, wherein:
   the photoelectric smoke sensor is provided with a smoke sensing portion which senses smoke in the sucked air, a suction port provided on the air inflow side of the smoke sensing portion, directly sucking the air in the region to be inspected, and fitting ports provided on the air outflow side of the smoke sensing portion and on opposite sides of a housing, each fitting port being fitted with an end portion of a section of the piping,
   the control unit sucks air though said piping and the air sucked through the piping causes air to be sucked from the suction port past the smoke sensing portion provided in each photoelectric smoke sensor,
   the smoke sensing portion of the photoelectric smoke sensor is provided with:
      said housing, into which air mixed with smoke flows;
      a light emitting element provided facing a detection region in the housing and emitting inspection light to the detection region;
      a light receiving element provided facing the detection region at a position deviated from an optical path of the inspection light of the light emitting element and receiving diffused light diffused by hitting of the inspection light with smoke and detecting the smoke; and
      a reflecting member which is provided in the housing and deviates and reflects the inspection light emitted from the light emitting element so that the inspection light does not enter the light receiving element, and
   a shielding plate which is provided between the light emitting element and the light receiving element and prevents incidence of the inspection light from the light emitting element directly into the light receiving element is brought closer to the light emitting element than to the light receiving element, and moreover, a focal distance of a lens of the light receiving element is made short so as to bring the light receiving element far away from the shielding plate and to widen a light incident angle of the light receiving element.

2. The suction-type smoke sensing system according to claim 1, wherein
   the control unit identifies a position of fire occurrence from positional information of the photoelectric smoke sensor which is a transmitting source of a received detection signal.

3. The suction-type smoke sensing system according to claim 1, wherein
   sensitivity of the smoke sensing portion of the photoelectric smoke sensor arranged in each of a plurality of the regions to be inspected is adjusted to optimal sensitivity in accordance with a situation of each region to be inspected.

4. The suction-type smoke sensing system according to claim 1, wherein
   the reflecting member is provided at a position opposing the light emitting element and the light receiving element sandwiching the detection region and reflects the inspection light from the light emitting element in a direction not toward the light receiving element.

5. The suction-type smoke sensing system according to claim 1, wherein
   the reflecting member is provided at a position opposing the light emitting element and the light receiving element sandwiching the detection region and reflects the inspection light from the light emitting element in a direction gathering to the detection region.

6. The suction-type smoke sensing system according to claim 1, wherein
a light amount of a light source of the light emitting element is increased and directivity thereof is enhanced.

7. The suction-type smoke sensing system according to claim 1, wherein
a labyrinth which prevents intrusion of ambient light and allows intrusion of smoke is provided in the housing and a projection portion of the labyrinth and a projection portion of an opening of the light receiving element are eliminated.

8. The suction-type smoke sensing system according to claim 1, wherein
the light receiving element is attached with a lens to a light receiving element accommodation portion, an inclined member is provided inside the lens in the light receiving element accommodation portion, and the inclined member is provided with an inclined surface which reflects reflected light incident to a periphery of the lens in the light receiving element accommodation portion to the outside of the light receiving element accommodation portion.

9. The suction-type smoke sensing system according to claim 1, wherein a number of the regions is greater than a one, and wherein at least one said photoelectric smoke sensor is provided for each of said regions.

10. The suction-type smoke sensing system according to claim 1, wherein the suction port is fitted with a base end portion of a suction pipe extending to the region to be inspected.

* * * * *